United States Patent
Bobnock

(10) Patent No.: US 8,242,056 B2
(45) Date of Patent: Aug. 14, 2012

(54) AGRICULTURE ACTIVES DELIVERY COMPOSITION COMPRISING BORON AND PERSULFATE ION-CROSSLINKED POLYVINYL ALCOHOL MICROCAPSULES AND METHOD OF USE THEREOF

(75) Inventor: Robert Stanley Bobnock, Menasha, WI (US)

(73) Assignee: Appleton Papers Inc., Appleton, WI (US)

( * ) Notice: Subject to any disclaimer, the term of this patent is extended or adjusted under 35 U.S.C. 154(b) by 317 days.

(21) Appl. No.: 12/587,669

(22) Filed: Oct. 9, 2009

(65) Prior Publication Data

US 2010/0099566 A1  Apr. 22, 2010

Related U.S. Application Data

(60) Provisional application No. 61/196,550, filed on Oct. 17, 2008.

(51) Int. Cl.
*A01N 59/00* (2006.01)
*A61K 9/50* (2006.01)
*A01N 59/14* (2006.01)

(52) U.S. Cl. ......... 504/358; 504/187; 424/490; 424/657

(58) Field of Classification Search ............... 504/358, 504/116
See application file for complete search history.

(56) References Cited

U.S. PATENT DOCUMENTS

| | | | | |
|---|---|---|---|---|
| 4,657,582 | A | 4/1987 | Huber | 71/121 |
| 5,599,767 | A * | 2/1997 | Lew et al. | 504/206 |
| 6,560,923 | B1 | 5/2003 | Kamei et al. | 47/64 |
| 2002/0098982 | A1 | 7/2002 | Burnham | 504/359 |
| 2005/0271727 | A1 * | 12/2005 | Yao | 424/486 |
| 2009/0227451 | A1 * | 9/2009 | Rose et al. | 504/100 |

\* cited by examiner

*Primary Examiner* — Johann Richter
*Assistant Examiner* — Erin Hirt
(74) *Attorney, Agent, or Firm* — Benjamin Mieliulis

(57) ABSTRACT

An aqueous composition is provided having a pH of from about 2.0 to about 12.8 and comprising boron or persulfate ion-crosslinked polyvinyl alcohol microcapsules. A method of delivering an agriculture active to a substrate is further provided comprising applying to the substrate an aqueous composition comprised of agriculture active containing, boron or persulfate ion-crosslinked, polyvinyl alcohol microcapsules, as well as a method of treating a substrate to protect from pests or promote crop growth comprising applying to the substrate an aqueous treating composition comprised of agriculture active containing, boron or persulfate ion-crosslinked, polyvinyl alcohol microcapsules.

20 Claims, No Drawings

AGRICULTURE ACTIVES DELIVERY COMPOSITION COMPRISING BORON AND PERSULFATE ION-CROSSLINKED POLYVINYL ALCOHOL MICROCAPSULES AND METHOD OF USE THEREOF

This application claims priority under 35 U.S.C. §119(e) to U.S. Provisional Application Ser. No. 61/196,550 filed Oct. 17, 2008.

BACKGROUND OF THE INVENTION

The present invention is directed to an agriculture actives delivery composition comprising boron or persulfate ion-crosslinked polyvinyl alcohol microcapsules and a method of use thereof.

Microcapsules have been known for many years and have many and varied uses. For instance, microcapsules have utility in the areas of carbonless paper, pressure sensitive adhesives, pressure sensitive indicators, and fragrance delivery compositions.

Many processes for microencapsulation are known. These include methods for capsule formation such as described in U.S. Pat. Nos. 2,730,456, 2,800,457; and 2,800,458. Other useful methods for microcapsule manufacture are include those described in U.S. Pat. Nos. 4,001,140; 4,081,376 and 4,089,802 describing a reaction between urea and formaldehyde; U.S. Pat. No. 4,100,103 describing reaction between melamine and formaldehyde; and British Patent No. 2,062,570 describing a process for producing microcapsules having walls produced by polymerization of melamine and formaldehyde in the presence of a styrenesulfonic acid. Microencapsulation is also taught in U.S. Pat. Nos. 2,730,457 and 4,197,346. Processes for forming microcapsules from urea-formaldehyde resin and/or melamine formaldehyde resin are disclosed in U.S. Pat. Nos. 4,001,140, 4,081,376; 4,089,802; 4,100,103; 4,105,823; 4,444,699. Alkyl acrylate-acrylic acid copolymer capsules are taught in U.S. Pat. No. 4,552,811.

Common microencapsulation processes can be viewed as a series of steps. First, the core material which is to be encapsulated is emulsified or dispersed in a suitable dispersion medium. This medium is preferably aqueous but involves the formation of a polymer rich phase. Frequently, this medium is a solution of the intended capsule wall material. The wall material is thereby contained in the liquid phase which is also dispersed in the same medium as the intended capsule core material. The liquid wall material phase deposits itself as a continuous coating about the dispersed droplets of the internal phase or capsule core material. The wall material is then solidified. This process is commonly known as coacervation.

Phase separation processes, or coacervation processes are described in U.S. Pat. Nos. 2,800,457 and 2,800,458. Encapsulations based on polymerization of urea and formaldehyde, monomeric or low molecular weight polymers of dimethylol urea or methylated dimethylol urea, melamine and formaldehyde, methylated melamine formaldehyde, monomeric or low molecular weight polymers of methylol melamine or methylated methylol melamine, are taught in U.S. Pat. No. 4,552,811. These materials are typically dispersed in an aqueous vehicle and the reaction is conducted in the presence of acrylic acid-alkyl acrylate copolymers.

Polyvinyl alcohol microcapsules are taught by U.S. Pat. Nos. 3,886,084; 4,244,836; 4,269,729; 4,898,781; 5,064,650; 5,225,117; and 5,246,603.

In addition, core-material microcapsules have been used for many years in a variety of compositions, including but not limited to cleaning compositions. Perfume-containing microcapsules have also been used for many years in compositions designed to counteract malodors. Such microcapsules may contain a variety of cleaning solution-compatible components, such as cleaning oils, fragrances, colorants, etc. For instance, when used in hard surface cleaners such as floor cleaners, such microcapsules typically are intended to be subjected to crushing or disintegrating force upon application to a substrate to permit release of the core material, such as a fragrant oil.

Delivery systems for agricultural actives typically cannot rely on crushing or pressure or physical force methods in many fields of use. For example, an agriculture active dispersed on a leaf structure requires preferably a mechanism other than crushing for release of core material.

A disadvantage with respect to the use of prior art microcapsules produced by the above methods in, for example, the imparting of a fragrance during the cleaning of hard surfaces is that the microcapsules are somewhat resistant to rupture. As a result, the deposition of such microcapsules (which include a fragrant core material) is less than effective, as the microcapsules do not rupture absent physical force being applied. The microcapsules can also migrate into the pores of any porous surfaces to which the cleaning product is applied so as to further resist rupture.

Similarly agriculture actives deposited on a surface in microcapsules can be less than effective if the agriculture active is not available at the time when it can be most effective. Availability can be hindered if release is too slow or the microcapsules do not release the core contents absent physical force being applied.

U.S. Pat. No. 5,064,650 discloses salt-sensitive microcapsules. U.S. Pat. No. 5,364,634 discloses pH sensitive microcapsules. U.S. patent publication 2004/0115091 discloses perfume-containing microcapsules which are ruptured by the application of physical force.

It is thus desirable to provide a method for the formation of microcapsules which are susceptible to rupture or disintegration in the absence of applied force under the desired conditions of use.

It is further desirable to provide an aqueous delivery composition for agriculture actives containing microcapsules that can be used with advantage wherein microcapsules contained therein are susceptible to rupture or disintegration in the absence of applied force under the desired conditions of use.

It is further desirable to provide a method of crop field application or agriculture active delivery comprising the use of a solution containing the agriculture actives containing microcapsules of the present invention which are susceptible to rupture or disintegration in the absence of applied force under the desired conditions of use.

OBJECTS AND SUMMARY OF THE INVENTION

It is accordingly an object of the present invention to provide microcapsules which are particularly useful as a core component delivery system in an aqueous agriculture actives delivery composition.

It is also an object of the present invention to provide microcapsules having particular utility in aqueous compositions such as crop field application or agriculture active delivery compositions.

It is still yet further an object of the present invention to provide a method of crop field application or agriculture actives delivery using the novel agriculture active delivery composition of the present invention.

In accordance with the present invention, there is thus provided a water-containing composition having a pH of from about 4.8 to about 12.8, or even from about 1.9 to about 12.8 and comprising boron or persulfate ion-crosslinked polyvinyl alcohol microcapsules.

In accordance with the present invention, there is also provided a method of protecting or enhancing field crops, comprising applying an agriculture active composition to the field or crop comprising an aqueous agriculture active composition having a pH of from about 6 to about 12, or even from 3 to about 12, and comprising an effective amount of at least one agriculture active component and boron ion-crosslinked agriculture active containing polyvinyl alcohol microcapsules.

In still further in accordance with the present invention, there is provided a method of delivering an agriculture to a substrate, field or crop comprising applying thereto an aqueous composition comprised of agriculture active containing, boron or persulfate ion-crosslinked, polyvinyl alcohol microcapsules, the microcapsules being temperature-sensitive and susceptible to disintegration in the absence of the application of crushing force upon drying of the composition subsequent to application of the composition to the substrate, field or crop (hereinafter understood as "substrate").

In accordance with a preferred embodiment of the present invention, the microcapsules of the present invention are prepared by a method comprising the steps of:
  (a) providing an aqueous suspension of polyvinyl alcohol having a solids content within the range of about 4 to about 25% by weight;
  (b) combining the aqueous suspension of step (a) with at least one emulsifiable agriculture active component under sufficient applied shear and for a time sufficient to obtain a stable emulsion of the at least one emulsifiable fragrance component in the aqueous suspension of polyvinyl alcohol; and
  (c) subsequently adding a source of boron or persulfate ions to the emulsion of step (b) in an amount and under conditions sufficient to cross-link the polyvinyl alcohol to obtain an aqueous mixture of agriculture actives containing microcapsules.

DETAILED DESCRIPTION OF THE INVENTION

The agriculture actives delivery composition of the present invention comprises an aqueous composition comprising boron ion-crosslinked polyvinyl alcohol-based agriculture active containing microcapsules having desirable thermal, salinity and pH sensitivity.

The microcapsules of the present invention are formed by a coacervation method where polyvinyl alcohol is deposited around droplets of an emulsifiable agriculture active component in aqueous suspension, with the polyvinyl alcohol subsequently being crosslinked by boron or persulfate ions.

More specifically, a stable emulsion of polyvinyl alcohol and at least one emulsifiable agriculture active component (such as a pesticide or herbicide oil) is formed, followed by the step of contacting the stable emulsion with a source of boron or persulfate ions to crosslink the polyvinyl alcohol to form a suspension of the desired polyvinyl alcohol-based microcapsules having an agriculture active core material.

The advantages of the present invention are many. For instance, it has been unexpectedly and desirably found that the microcapsules produced by the method of the present invention exhibit thermal and/or pH sensitivity. Such thermal and/or pH sensitivity enables the microcapsules to disintegrate and release the fragrant core material contained therein under destabilizing conditions of temperature and/or pH. The microcapsules can be caused to rupture by changing the salinity of the solution to which they are exposed, by letting them dry naturally, or by changing the pH of the solution (such as contact with a substrate of particular pH). Little or no heat is required to produce the microcapsules. The use of polyvinyl alcohol is also an advantage in that it serves both as an emulsifier, and as a wall material for the microcapsule, thus often avoiding the need for the use of separate emulsifiers and encapsulating materials. Milling (or stirring) times are also greatly shortened to 5 minutes or less. Further, the microcapsules of the present invention disperse readily in either cationic or anionic systems.

That is, such microcapsules, once removed from the aqueous medium in which they are formed and in which they exhibit relative structural stability under ambient conditions and a pH of from 2.0 to 13, are particularly susceptible to changes in temperature and/or pH such that, upon exposure to same, readily rupture or disintegrate and release the content of the microcapsule. As discussed in greater detail below, such microcapsules have particular utility in agricultural products for applications to soil or leaves or seeds or other plant structures where the microcapsules rupture and/or degrade subsequent to application and the agricultural active core material is released, as well as in applications where it is desired to apply an agriculture active component to a substrate.

In the present invention, the agriculture active core material is enclosed by a polyvinyl alcohol coating material.

Polyvinyl alcohol and its derivatives used in this invention include completely saponified polyvinyl alcohol, partially saponified polyvinyl alcohol, anion-modified polyvinyl alcohol, and the like. The use of polyvinyl alcohol as a core coating material in the formation of microcapsules is known to those skilled in the art. See the previously-mentioned U.S. Pat. Nos. 3,886,084; 4,244,836; 4,269,729; 4,898,781; 5,064,650; 5,225,117; and 5,246,603, among others.

Various modified polyvinyl alcohols can also be used as the coating material. Examples of such modified polyvinyl alcohols which are advantageously usable in this invention include, but are not limited to, cation modified polyvinyl alcohols obtained by the treatment with, for example, dimethyl aminopropyl acrylamide and methyl chloride; alkyl modified polyvinyl alcohols obtained by the treatment with, for example, vinyl versatate (VEOVA); acid modified polyvinyl alcohols obtained by the treatment with, for example, acrylic acid or itaconic acid; and acetacetylated modified polyvinyl alcohols using, for example, diketenes.

Suitable polyvinyl alcohol polymers which can be used in the present invention include those containing not less than 60 mol % total of vinyl alcohol units and vinyl acetate units and having a cloud point when formulated into aqueous solutions. For example, suitable polymers include partially saponified polyvinyl alcohols having saponification degrees of 60 to 80 mol %; completely or partially saponified, modified polyvinyl alcohols obtained by the introduction of 0.1 to 20 mol % of ethylene and/or an olefin having a long chain alkyl group of 3 to 20 carbon atoms into the polymer by copolymerization and/or by modification of the polymer after the polymerization reaction; partially saponified, modified polyvinyl alcohols obtained by introduction of 0.1 to 5 mol % of a hydrophilic group into the polymer by copolymerization; partially or completely saponified, modified polyvinyl alcohols obtained by the introduction of 0.1 to 20 mol % of a hydrophilic group and 0.1 to 20 mol % of ethylene and/or an olefin having a long chain alkyl group of 3 to 20 carbon atoms into the polymer by copolymerization and/or by modification of the polymer after the polymerization reaction; partially or completely saponified polyvinyl alcohols having a lactone ring content of 1 to 40 mol %; etc.

These polyvinyl alcohol polymers can be prepared by: (1) polymerizing vinyl acetate alone, followed by saponification; (2) copolymerizing vinyl acetate with at least one comonomer selected from the group of ethylene, olefinically unsaturated compounds each having a long chain alkyl group and olefinically unsaturated, hydrophilic-group-containing compounds, followed by saponification; (3) polymerizing vinyl acetate alone or copolymerizing vinyl acetate with an olefinically unsaturated compound having a hydrophilic group, followed by saponification and by subsequent acetalization, esterification and/or etherification with an aldehyde, acid and/or alcohol each having a long chain alkyl group; (4) copolymerizing vinyl acetate with an olefinically unsaturated compound having a carboxyl or carboxylate ester group, followed by saponification and by subsequent acid or heat treatment, and other methods.

Suitable examples of olefinically unsaturated compounds which have a long chain alkyl group are alpha olefins such as 1-octadecene, 1-hexadecene, 1-dodecene and 1-octene; vinyl esters such as vinyl stearate, vinyl laurate, vinyl versatate and vinyl propionate; acrylate esters such as stearyl acrylate, lauryl acrylate, octyl acrylate and butyl acrylate; methacrylate esters such as stearyl methacrylate, lauryl methacrylate, octyl methacrylate and butyl methacrylate; vinyl ethers such as stearyl vinyl ether, lauryl vinyl ether and butyl vinyl ether, and similar compounds having a long chain alkyl group of 3-20 carbon atoms in the side chain.

Suitable examples of olefinically unsaturated compounds having a hydrophilic group are, for example, carboxyl-containing compounds such as acrylic acid, methacrylic acid, maleic acid, maleic anhydride, itaconic acid and fumaric acid and esters thereof; sulfonic acid compounds such as vinylsulfonic acid and allylsulfonic acid, esters and alkali metal salts thereof; and nitrogen-containing compounds such as vinylpyrrolidone, acrylamide, N-substituted acrylamides and vinyl pyridine.

Suitable examples of the above described olefinically unsaturated compounds having a carboxyl or carboxylate ester group include acrylic acid, methacrylic acid, maleic acid, maleic anhydride, itaconic acid and fumaric acid, and esters thereof.

Suitable examples of aldehydes, acids, and alcohols which have a long chain alkyl group for use in the modification of the vinyl polymer after polymerization include stearic acid, stearylaldehyde, stearyl alcohol, lauric acid, laurylaldehyde, lauryl alcohol, butyric acid, butyraldehyde, butanol, etc.

A number of polyvinyl alcohol polymers suitable for use in the present invention are commercially available, such as partially hydrolyzed Celvol 523, 502, 205, 203 and 540.

The specific temperatures used in the microencapsulation process are determined by the varying properties of the polyvinyl alcohol polymer used and/or by variations in the concentration of the polyvinyl alcohol polymer in the aqueous solution. Generally, however, a temperature within the range of from about 20 to about 85° C. is employed during the crosslinking process. One advantage of the present invention is that the crosslinking process may occur under ambient conditions in the absence of added heat input, while also occurring under a period of time less than what would normally be expected.

The pH of the solution during crosslinking is generally maintained within the range of from about 2 to about 10. It has been found that the resulting boron or persulfate ion-crosslinked polyvinyl alcohol microcapsules are relatively stable under such conditions of temperature and pH.

In the present invention, the concentration of the polyvinyl alcohol polymer in the aqueous solution is generally maintained within the range of 3 to 25 weight % at the time of phase separation. It is also possible, however, (1) to use an aqueous solution of greater polyvinyl alcohol polymer concentration in the dispersion step to increase the efficiency of this step and then adjust the concentration to the desired level by dilution of the solution, or (2) to use a more dilute aqueous polyvinyl alcohol polymer solution in the dispersion step and then adjust the concentration in the phase separation step upward by gradually adding a concentrated aqueous solution of the polyvinyl alcohol polymer to the dilute solution.

With regard to the method employed for treating the wall membranes of the capsules to solidify the same, a boron or persulfate ion is used which is capable of reacting with the polyvinyl alcohol polymer which results in substantial crosslinking/solidification of the separated phase of the polyvinyl alcohol polymer in the aqueous emulsion. Suitable boron ion-sources include boric acid and borates such as Borax, ulexite, colemanite, sodium tetraborate, sodium metaborate, calcium borate disodium tetraborate peutahydrate, disodium tetraborate decahydrate, disodium tetraborate sodium metaborate, sodium perborate, and perborate silicate. The term "borate" includes salts or esters of boric acid and includes any compound possessing a borate group which is capable of complexing with the polyvinyl alcohol emulsifying agent in solution to form an impermeable coating. The walls of the microcapsules of the present invention are formed of non-metallic bonds. Boron is considered to be a non-metallic element as defined in The Van Nostrand Chemist's Dictionary, D. Van Nostrand Company, Inc., (1953).

The persulfate ion source can include various peroxy monosulfates and peroxydisulfates. More particularly the persulfate ion source can include alkali peroxymonosulfates, alkaliperoxydisulfates, ammonium peroxydisulfates. A common alkali peroxydisulfate is potassium persulfate also known as dipotassium persulfate or potassium peroxydisulfate. Sodium persulfate is also useful, and is also known as sodium peroxydisulfate and disodium peroxydisulfate.

The crosslinking or complexing boron or persulfate-containing agent is utilized in amounts sufficient to result in the formation of microcapsules. The relative amounts vary with the particular system, and may be easily determined in each case. The polyvinyl alcohol emulsifying agent is dual functional, and serves not only as an emulsifying agent, i.e., to stabilize the surface of the emulsifiable fragrance component and prevent coalescense, but actually provides the shell. Thus, the polyvinyl alcohol emulsifying agent should be provided in relatively substantial amounts of, for example, at least about 0.5 part by weight per part of boron ion crosslinking or complexing agent. Suitable amounts include, for example, between about one and about 100 parts of polyvinyl alcohol, preferably between about one and about 20 parts polyvinyl alcohol, per part by weight of boron ion crosslinking or complexing agent.

A variety of agriculture active core components may be employed with advantage in the present invention, the selection of which is well within the ability of one skilled in the art. Suitable components include those capable of being emulsified and encapsulated by the polyvinyl alcohol polymer of the present invention, and which are either substantial insoluble in water or which can be made water insoluble or less water soluble such as at certain pHs in order to permit the requisite emulsion to be formed.

Internal phase oils, or oil phase, or oil solvent or organic solvents or "nonsolvent for the water phase," are used interchangeably for purposes hereof Typical organic solvents for the core, are typically nonsolvent for the water phase, and are used in an amount sufficient for emulsifying the agriculture actives, and may include various solvents such as mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, 3-methoxy-3-methyl-butanol, alkanediols, propylene glycols, various alcohols, essential oils, and blends of any of the foregoing with alcohols or various diluents. The solvent for the core material and the agriculture active of the core is each independently selected to be somewhat or substantially water insoluble or water insoluble to a degree or able to be made substantially water insoluble at certain pH's. The purpose of the organic solvent is to facilitate emulsifying the core material by solubilizing or dispersing the desired agricultural core and/or partitioning the core material from the water in the capsule formation process. Other useful solvents for the core include vegetable oils such as canola oil, soybean oil, corn oil, cottonseed oil, alkyl esters of fatty acids, transesterified vegetable oils such as transesterified canola oil, soybean oil, corn oil, cottonseed oil, sunflower oil, methyl ester of oleic acid, parafinnic aliphatic hydrocarbons The liquid core material or solvent for the agriculture active employed in the microcapsules can be any material which is liquid within the temperature range at which the capsules are formed. Examples of eligible oil solvent liquids also include, but are not limited to various conventional organic solvents including ethyldiphenylmethane (U.S. Pat. No. 3,996,405); benzylxylene (U.S. Pat. No. 4,130,299); alkyl biphenyls such as propylbiphenyl (U.S. Pat. No. 3,627,5810; butylbiphenyl (U.S. Pat. No. 4,287,074); dialkyl phthalates in which the alkyl groups thereof have from 4 to 13 carbon atoms, e.g. dibutyl phthalate, dioctylphthalate, dinonyl phthalate and ditridecylphthalate; 2,2,4-trimethyl-1,3-pentanediol diisobutyrate (U.S. Pat. No. 4,027,065); $C_{10}$-$C_{14}$ alkyl benzenes such as dodecyl benzene; alkyl or aralkyl benzoates such as benzyl benzoate; alkylated naphthalenes such as dipropylnaphthalene (U.S. Pat. No. 3,806,463); partially hydrogenated terphenyls; high-boiling straight or branched chain hydrocarbons; and mixtures of the above. The solvents for the agriculture active can include any of the above or the like which possess sufficient solubility for the agriculture active material. Common diluents such as straight chain hydrocarbons can also be blended with any of the solvents, or blend of solvents. The solvent is selected on the basis of hydrophobicity and ability to disperse or solvate the agriculture active material. The internal phase oil ends up as the core or internal contents of the microcapsule along with the agriculture active material.

In an alternate aspect the agriculture active material forming the core can be a fraction of the core or 100 weight percent of the core such as when the core is selected to be an essential oil, rather than an optional additional solvent. The weight percent of the agriculture active in the core is selected to be sufficient to provide bioavailability for the targeted control effect and is readily determinable by the skilled artisan.

The term agriculture actives are meant to include any compound that directly or indirectly has a beneficial effect on a plant or its propagation material. The terms agriculture active and agriculture actives are used interchangeably and are intended to include herbicides, pesticides, fertilizers, growth factors, nutrients, and the like. Optionally the agriculture active can be applied to soil, or to surrounding or other surfaces. Agriculture active is not intended to be restricted or limited to application just to plants, but used in its broad sense. Substrates and surfaces appropriate for application of the microcapsules of the invention include soil, fields, walls, carpeting, painted surfaces, plasters, concretes, timbers, insulation, as well as plants, crops, roots, seeds and the like.

An agriculture active material suitable for use in the present invention is defined as being any material having a beneficial effect on a plant or its propagation material which may be incorporated into the microcapsule of the present invention by means of the method of encapsulation of the present invention.

Useful agricultural actives in the present invention include materials selected from the group consisting of pesticides, herbicides and growth regulators. Pesticide for purposes hereof includes insecticides and insect repellants. Examples of useful actives include by way of illustration and not limitation, acylalanines, alkanamides, amidines, anilides, anilinopyrimidines, aromatic hydrocarbons, chlorophenyls, arylaminopropionic acids, aryloxyalkanoic acids, aryloxyalkanoic acids, aryloxyphenoxypropionates, auxins, avermectins, benzamides, benzenecarboxilic acids, benzilates, benzimidazoles, benzofurans, benzoic acids, benzonitriles, benzothiadiazinones, benzothiazolones, benzotriazines, benzoylureas, bipyridyliums, biscarbamates, butyrolactones, carbamates, carbamoyltriazoles, chloroacetamides, chloronitriles, chloronicotinyls, cinnamic acids, coumarin anticoagulants, cyclodiene organochlorines, cyclohexanedione oximes, cytokinins, diacylhydrazines, dicarboximides, 2-dimethylaminopropane-1,3-dithiols, dimethyldithiocarbamates, dinitroanilines, dinitrophenols, diphenyl ethers, dithiocarbamates, DMI:imidazoles, DMI:pyridines, DMI:pyrimidines, DMI:triazoles, gibberellins, glycine derivatives, guanidines, halogenated alkanoic acids, hydroxyanilides, hydroxylbenzonitriles, imidazoles, imidazolinones, indandione anticoagulants, isoxazoles, isoxazolidinones, juvenile hormone mimics, MBI:dehydrases, morpholines, multi-site: alkylenebis(dithiocarbamates), multi-site: chloronitriles, multi-site: dimethyldithiocarbamates, multi-site: guanidines, multi-site: inorganics, multi-site: phenylphridinamines, multi-site: phosphonates, multi-site: phthalimides, multi-site: quinones, multi-site: sulphamides, natural pyrethrins, neonicotinoids, nitromethylene: neocorticoids, non-ester pyrethroids, N-phenyl carbamates, N-phenylphthalimides, organoarsenics, organochlorines, organophosphorous compounds, organotins, oxadiazines, oxadiazoles, oxathlins, oxozolidinediones, oxazolidinones, oxime carbamates, oxyacetamides, phanylamide: acylalanines, phenylamide: butyrolactones, phenylamide: oxazolidinones, phenylpyrazole herbicides, phenypyrazole insecticides, phenylpyridazines, phenylpyridinamines, phenylpyrroles, phenylureas, pheromones, phosphinic acids, phosphonates, phosphoroamidates, phosphorodithioates, phosphorothiolates, phthalamates, phthalimides, piperazines, polyoxins, pyrazoles, pyrazoliums, pyrethrins, pyrethroids, pyrethroid non-esters, pyridazinones, pyridazinones, pyridazinone analogues, pyridines, pyridinecarboxamides, pyridinecarboxylic acids, pyrimidindiones, pyrimidines, pyrimidinols, pyrimidinyl carbinols, pyrimidinyloxybenzoic compounds, pyrimidinyloxybenzoic analogues, quaternary ammonium compounds, quinolines, quinolinecarboxylic acids, quinones, semi-carbazones, strobilurin type compounds, sulfonylaminocarbonyltriazolinones, sulfonylureas, sulfamides, synthetic auxins, tetrazines, tetrazolinones, thiadiazoles, thiocarbamates, 1,3,5-triazines, 1,2,4-triazinones, triazoles, triazolinones, triazolpyrimidines, triketones, uracils and ureas.

Examples of useful strobilurin type compounds include metominostrobin, picoxystrobin, famoxadone, azoxystrobin, kresoxim-methyl and trifloxystrobin.

Examples of useful neonicotinoids include acetamiprid, imidacloprid and thiamethoxam.

Examples of useful herbicides include phenoxy acetic acids, such as 2,4-D and MCPA; phenoxy propionic acids, such as dichlorprop (2,4-DP) and mecoprop (MCPP); phenoxy butyric acids, such as 2,4-DB and MCPB; benzoic acids, such as dicamba (Banvel, Clarity, Vanquish); picolinic acid and related compounds, such as picloram (Tordon), triclopyr (Garlon, Grandstand, Remedy, Turflon); clopyralid (Lontrel, Reclaim, Stinger, Transline), and quinclorac (Facet); naptalam (Alanap); semicarbones, such as diflufenzopyr-sodium (BAS 654, Distinct); chloro-s-triazines, such as atrazine (Aatrex, Atrazine), simazine (Princep), and cyanazine (Bladex); methoxy-s-triazines, such as prometon (Pramitol); methylthio-s-triazines, such as ametryn (Evik), and prometryn (Caparol, Cotton-Pro, Gesagard); other triazines, such as hexazinone (Velpar), and metribuzin (Sencor, Lexone); substituted ureas, such as diuron (Karmex), fluometuron (Cotoran), linuron (Lorox), and tebuthiuron (Spike); uracils, such as bromacil (Hyvar), and terbacil (Sinbar); benzothiadiazoles, such as bentazon (Basagran); benzonitriles, such as bromoxynil (Buctril); phenylcarbamates, such as desmedipham (Betanex), and phenmedipham (Spin-aid); pyridazinones, such as pyrazon (Pyramin); phenypyriddazines, such as pyridate (Tough, Lentagran); propanil (Stam, Stampede); amitrole (Amitrol T); clomazone (Command); fluridone (Sonar); pyridazinones, such as norflurazon (Zorial, Evital, Solicam, Predict); isoxazoles, such as isoxaflutole (Balance); dinitroanilines, such as benefin (Balan), ethalfluralin (Sonalan, Curbit), oryzalin (Surflan), pendimethalin (Prowl, Pendulum, Pentagon), prodiamine (Barricade, Endurance, Factor), and trifluralin (Treflan Trifluralin); pyridines, such as dthiopyr (Dimension), and thiazopyr (Visor); amides, such as pronamide (Kerb); DCPA (Dacthal); carbamothioates (thiocarbamates), such as EPTC (Eptam, Eradicane, Eradicane Extra), cycloate (Ro-Neet), pebulate (Tillam), and triallate (Far-Go, Avandex BW), butylate (Sutan+), molinate (Ordram), thiobencarb (Bolero, Abolish), and vernolate (Vernam); seedling root inhibiting amides, such as napropamide (Devrinol); seedling root inhibiting phenylureas, such as siduron (Tupersan); bensulfide (Prefar, Betasan, Bensumec); chloroacetamides, such as acetochlor (Harness, Surpass, Topnotch); dimetenamid (Frontier), propachlor (Ramrod); alachlor (Lasso, Micro-Tech, Partner), and metolachlor (Dual, Pennant); glyphosate (Roundup, Rodeo); sulfosate (Touchdown); sulfonylureas, such as bensulfuron (Londax), chlorsulfuron (Glean, Telar), halosulfuron (Permit, Battalion, Manage), nicosulfuron (Accent), prosulfuron (Peak), rimsulfuron (Matrix, Elim, Titus, Prism), thifensulforon (Pinnacle), tribenuron (Express), chlorimuron (Classic), ethametsulfuron (Muster), metsulfuron (Ally, Escort), primisulfuron (Beacon), oxasulfuron (Expert), triasulfuron (Amber), and triflusulfuron (Upbeet); imidazolinones, such as imazamethabenz (Assert), imazamox (Raptor), imazapic (Cadre, Contend), imazapyr (Arsenal, Chopper, Stalker), imazaquin (Scepter, Image) and imazethapyr (Pursuit); aryoxyphenoxyproprionates, such as diclofop-methyl (Hoelon, Hoe-Grass, Illoxan), fenoxaprop-ethyl (Acclaim, Horizon, Excel), fenoxaprop-p-ethyl (Option II, Puma, Whip 360, Horizon), fluazifop-p-butyl (Flusilade 2000), haloxyfop (Verdict, Gallant), and quizalofop-p-ethyl (Assure II); cyclohexanediones, such as clethodim (Envoy, Prism, Select), sethoxydim (Poast, Poast Plus, Prestige, Torpedo, Ultims, Vantage), and tralkoxydim (Achieve); nitriles, such as dichlobenil (Casoron, Dyclomec); benzamides, such as isoxaben (Gallery); quinclorac (Facet); dilute sulfuric acid; monocarbamide dihydrogen sulfate (Enquick); herbicidal oils; bipyridyliums, such as diquat (Diquat, Reward), and paraquat (Gramoxanone Extra, Cyclone, Starfire); diphenylethers, such as acifluorofen (Blazer, Status), fomesafen (Flexstar, Reflex), lactofen (Cobra), and oxyfluorfen (Goal); oxidiazoles, such as fluthiacet (Action), and oxadiazon (Ronstar); n-phenylheterocycles, such as carfentrazone (Affinity, Aim), flumiclorac (Resource), and sulfentrazone (Authority, Cover, Spartan); glufosinate (Finale, Liberty, Rely); organic arsenicals, such as DSMA, and MSMA; asulam (Asulox); endothall (Accelerate, Aquathol, Des-I-Cate); ethofumesate (Nortron, Prograss); fosamine (Krenite); difenzoquat (Avenge); and TCA (Nata).

Examples of useful fungicides and fungicidal mixtures include fludioxonil, fluquinconazole, silthiopham, difenoconazole, a mixture of fludioxonil and fluquinconazole or 4,5-dimethyl-N-2-propenyl-2-(trimethylsilyl)-3-thiophencarboxamid; a mixture of difenoconazole and fluquinconazole or 4,5-dimethyl-N-2-propenyl-2-(trimethylsilyl)-3-thiophencarboxamid; and a mixture as taught in WO 00/27200 of a thienol[2,3-d]pyrimidin-4-one and an azole fungicide, an anilinopyrimidine fungicide, a morpholine fungicide, a strubilurin compound, a pyrrole compound, a phenylamide, or a dithiocarbamate fungicide.

A preferred material is sulfonyl urea such as nicrosulfuron. With sulfonyl urea, solubility is low when the pH of the dispersing solution is below the pKa and high when the pH is above the pKa. Sulfonylurea pKa values range from about 3.3 to 5.2 with nicosulfuron being half ionized and half un-ionized at its pKa of 4.3. Water solubility of nicrosulfuron is reported as 360 ppm at pH5, 12,200 ppm at pH 6.9 and 29,200 ppm at pH 8.8. Most sulfonylurea herbicides are available as dry formulations that readily disperse in solvent and blends with adjuvants such as starches, gels, gelatins, nonionic surfactants, buffers, ammonium salts, alkaline buffered methylated seed oil, nitrogen based fertilizer, and antifoam agents to modify retention or rate of evaporation. Solubilizing the sulfonylurea at the point of application can increase bioavailability, increase activity and provide more beneficial affect. The microcapsule system of the invention advantageous enables delivery to the site of application of capsules with dispersed or solubilized agriculture active core.

Preferred agricultural actives also include imidacloprid, acetamiprid, sulfonylurea, thiamethoxam, TI-435 (clothiamidin), simeconazole, fluquinconazole, tebuconazole, silthiopham, terbufos, chlorpyrifos, fipronil, chlorethoxyfos, tefluthrin, fipronif, carbofuran, tebupirimfos, methoprene, hydroprene, and mixtures thereof Imidacloprid and/or sulfonylurea has been found to be particularly preferred as the agricultural active of the present invention. Also preferred are various essential oils described below.

Thus, the compositions of the present invention may contain as active ingredients substantially purified .beta.-diones or crude .beta.-dione-containing extracts obtained from a volatile oil-bearing organism, preferably a volatile oil-bearing plant. Volatile oils, also known in the art as essential oils, typically comprise a volatile mixture of esters, aldehydes, alcohols, ketones and terpenes, which can be prepared from botanical materials or plant cell biomass from cell culture. Volatile oils can be prepared by subjecting botanical materials to a distillation process, for example. A number of different procedures can be used for distillation. For example, plant matter (e.g., foliage, stems, roots, seeds, bark etc) of a volatile oil-bearing plant is placed in a suitable still and steam distillation is used to break down the cells of the plant to release the oil. The steam is then condensed and the oil phase is separated from the aqueous phase to obtain the volatile oil. It will be appreciated that other methods of volatile oil extraction (e.g., solvent extraction) are known to those of skill in the art and it will be understood, in this regard, that the present invention is not limited to the use or practice of any one particular method of extracting volatile oils.

Suitably, the compositions comprise naturally-occurring compounds derived from a volatile oil-bearing organism. Thus, in a preferred embodiment, the pesticidal composition of the invention comprises one or more .beta.-dione active compounds, particularly .beta.-diketone- and/or .beta.-triketone-active compounds, that are derived from the volatile oil of a volatile oil-bearing organism. In this embodiment, the composition may optionally contain a naturally-occurring carrier and/or other naturally-occurring additives.

Naturally-occurring additives contemplated by the present invention include natural antioxidants, which can be used advantageously to reduce the effect of oxidation of the Compounds of the invention. An example of a suitable naturally-occurring antioxidant is .alpha.-tocopherol. Other additives, such as naturally-occurring stabilisers, are also contemplated, which may desirably be added to improve the stability and shelf life of the composition. Examples of suitable natural stabilisers include gum arabic, guar gum, sodium caseinate, polyvinyl alcohol, locust bean gum, xanthan gum, kelgum, and mixtures thereof In an alternate embodiment, the naturally-occurring compounds derived from a volatile oil may be modified or derivatised to improve, for instance, their shelf-life, stability, activity and/or bioavailability.

The compounds of the present invention are useful for controlling harmful, annoying or undesired pests. They may be used singularly or in combination with other pest-controlling compounds of the invention. By "controlling" is meant preventing, combating, eradicating, destroying, repelling, or mitigating pests or increasing the mortality or inhibiting the growth and/or development of pests. The term "pest" is used herein in its broadest sense and includes within its scope insects, arachnids (e.g., acari, spiders), helminths (e.g., nematodes), molluscs, protozoa (e.g., *Plasmodium* sp. *Paramecium* sp.), viruses (e.g., herpesviruses) and the like. Suitable applications for such control include, but are not limited to, combating and/or eradicating infestations by pests in animals (including humans) and/or plants (including trees) and/or stored products, which includes the administration to the animal or site of an effective quantity of a compound of the invention.

By "effective amount" is meant the administration or application of that amount of active compound, either in a single dose or as part of a series, that is effective for controlling a significant number of pests. Thus, for example, a "pesticidally-effective" amount is the amount of active compound that is effective for increasing the mortality or decreasing the growth of a significant number of pests. Alternatively, a "pest-repelling" effective amount is the amount of active compound that is noxious to, and/or induces behavioural changes in, a significant number of pests. The effective amount will vary depending upon the taxonomic group of pest exposed to the active compound, the formulation of the composition, and other relevant factors. It is expected that the amount will fall in a relatively broad range that can be determined through routine trials.

Accordingly, the compounds of the present invention can be used as pesticides, such as but not limited to insecticides, arachnicides, anti-helminthics, molluscicides antivirals, anti-protozoals and the like, or as pest repellents including repellents of insects, arachnids, helminths, molluscs, protozoa and viruses. In especially preferred embodiments, the compounds of the present invention are used in the control of insects, arachnids, helminths or molluscs. In practice, the compounds can be applied as formulations containing the various adjuvants and carriers known to or used in the industry for facilitating bioavailability, stability and dispersion. The choice of formulation and mode of application for any given compound may affect its activity, and selection will be made accordingly.

In general, a pest-controlling compound of the invention can be compounded with appropriate inert carriers and additives in an appropriate ratio by means of dissolving, separating, suspending, mixing, impregnating, adsorbing or precipitating operation to formulate into oil formulations, emulsifiable concentrates, wettable powders, flowables, granules, powders, dusts, solutions, suspensions, emulsions, controlled-release forms such as microcapsules, aerosols or fumigants. Typically, the compounds of the present invention can be mixed with a solid carrier, liquid carrier or gas carrier, optionally together with a surfactant and other adjuvants useful for such formulations.

The compounds of the invention can be used in an amount from about 0.00005% to about 95% by weight as contained in these formulations as their active component. As used herein, the term "about" refers to a quantity, level, value or amount that varies by as much as 30%, preferably by as much as 20%, and more preferably by as much as 10% to a reference quantity, level, value or amount.

Where the compounds are in the form of .beta.-dione-containing extracts, the formulations will usually comprise as their principal active ingredient from about 0.0001% to about 90%, preferably from about 0.0001% to about 50%, more preferably from about 0.0005% to about 10%, even more preferably from about 0.0005% to about 5%, even more preferably from about 0.0005% to about 1% and still even more preferably from about 0.001% to about 0.5% by weight of the extract.

Alternatively, where the compounds are in the form of substantially purified preparation of .beta.-diones, the formulations will usually comprise as their principal active ingredient from about 0.00005% to about 90%, preferably from about 0.0001% to about 50%, more preferably from about 0.0005% to about 10%, even more preferably from about 0.001% to about 5% and still even more preferably from about 0.001% to about 1% by weight of the substantially purified .beta.-dione.

By "substantially purified" is meant a compound which has been separated from components that naturally accompany it. Typically, a compound is substantially pure when at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., by chromatography or HPLC analysis.

Examples of solid carriers useful in preparing the formulations are clays including kaolin clay, diatomite, water-containing synthetic silicon oxide, bentonite, Fubasami clay, and acid clay; talcs; ceramics; inorganic minerals such as Celite, quartz, sulfur, active carbon, calcium carbonate and hydrated silica; and chemical fertilisers such as ammonium sulfate, ammonium phosphate, ammonium nitrate, urea and ammonium chloride, these solid carriers being finely divided or granular. Examples of useful liquid carriers are water, alcohols such as methanol and ethanol, ketones such as acetone and methyl ethyl ketone, aromatic hydrocarbons such as benzene, toluene, xylene, ethylbenzene and methylnaphthalene, aliphatic hydrocarbons such as hexane, cyclohexane, kerosene and light oil, esters such as ethyl acetate and butyl acetate, nitriles such as acetonitrile and isobutyronitrile, ethers such as diisopropyl and dioxane, acid amides such as N,N-dimethylformamide and N,N-dimethylacetamide, halogenated hydrocarbons such as dichloromethane, trichloroethane and carbon tetrachloride, dimethyl sulfoxide, and fish oils, mineral oils, plant derived oils such as canola oil, cottonseed oil, soybean oil and sesame oil as well as essential oils such as lavender oil, eucalyptus oil, tea tree oil, citrus oil etc. Solid or liquid carriers can be used alone or in combination. Examples of gas carriers, i.e., those of propellants, are butane gas, LPG (liquefied petroleum gas), dimethyl ether, fluorocarbons and carbon dioxide gas.

Optionally, a pigment or chromogen can be included in the capsules to provide a color changing mechanism and aid in identification or marking of substrate areas onto which the microcapsules have been coated, dispersed or otherwise applied or incorporated.

Chromogenic materials can include without limitation phthalide, leucauramine and fluoran compounds. Chromogens also include Crystal Violet Lactone (3,3-bis(4-dimethylaminophenyl)-6-dimethylaminophthalide, U.S. Pat. No. RE. 23,024); phenyl-, indol-, pyrrol- and carbazol-substituted phthalides (for example, in U.S. Pat. Nos. 3,491,111; 3,491, 112; 3,491,116; 3,509,174); nitro-, amino-, amido-, sulfonamido-, aminobenzylidene-, halo-, anilino-substituted fluorans (for example, in U.S. Pat. Nos. 3,624,107; 3,627,787; 3,641,011; 3,642,828; 3,681,390); Spiro-dipyrans (U.S. Pat. No. 3,971,808); and pyridine and pyrazine compounds (for example, in U.S. Pat. Nos. 3,775,424 and 3,853,869). Other eligible chromogenic materials include: 3-diethylamino-6-methyl-7-anilino-fluoran (U.S. Pat. No. 3,681,390); 2-anilino-3-methyl-6-dibutylamino-fluoran (U.S. Pat. No. 4,510,513) also known as 3-dibutylamino-6-methyl-7-anilino-fluoran; 3-dibutylamino-7-(2-chloroanilino)fluoran; 3-(N-ethyl-N-tetrahydrofurfurylamino)-6-methyl-7-3-5'6-tris(di-methylamin-o)spiro[9H-fluorene-9'1(3'H)-isobenzofuran]-3'-one; 7-(1-ethyl-2-methylindol-3-yl)-7-(4-diethylamino-2-ethoxyphenyl)-5,7-dihy-drofuro[3,4-b]pyridin-5-one (U.S. Pat. No. 4,246,318); 3-diethylamino-7-(2-chloroanilino)fluoran (U.S. Pat. No. 3,920,510); 3-(N-methylcyclohexylamino)-6-methyl-7-anilino-fluoran (U.S. Pat. No. 3,959,571); 7-(1-octyl-2-methylindol-3-yl)-7-4-(4-diethylamino-2-ethoxy-phenyl)-5,7-d-ihydrofuro[3,4-b]pyridin-5-one; 3-diethylamino-7,8-benzofluoran; 3,3-bis(1-ethyl-2-methylindol-3-yl)phthalide; 3-diethylamino-7-anilino-fluoran; 3-diethylamino-7-benzylamino-fluoran; 3'-phenyl-7-dibenzylamino-2,2'-spiro-di-[2H-1-benzo-pyran]; 6'[ethyl(3-methylbutyl)amino]-3'-methyl-2'(phenylamino)-spiro[isobenzofuran-1(3H), 9'-[9H]xanthen]-3-one; 6-(dimethylamino-3,3-bis(4-(dimethylamino)phenyl)-1 (3H)-isobenzofuranone (crystal violet lactone); 3-diethylamino-6-methyl-7-(2,4-dimethylphenyl)aminofluoran and the like and mixtures of any of the foregoing. The above identified patents are incorporated herein by reference as if fully set forth herein.

Alternatively the chromogen can comprise an acid-base indicator. Optionally it be selected to be colorless at an original pH. The substrate pH, whether acidic or basic can be relied on to produce a characteristic color change of the acid-base indicator. Optionally an activating solution causing a change in pH can be separately applied such as by over-spraying. The color change can be made visible, or alternatively fleeting, meaning visible until the activating solution dries at which time the color change can reverse. By appropriate selection of chromogen, either a more permanent color or fleeting color indication can be obtained, as desired.

Chromogenic material selected to be an acid-base indicator may be any commonly used acid-base indicator. Examples of acid-base indicators include phenolphthalein, thymolphthalein, fluorescein, o-cresophthalein, alpha-naptholphthalein, and combinations thereof These colorformers are colorless at low or acidic pH and exhibit a color change at a high or basic pH. In contrast many flouran type colorformers can be used as acidic indicators, colorless at high pH and exhibiting color at low or acidic pH. The chromogenic material can be selected to be color indicating at a desired target pH by appropriate selection of either acid or base or neutral pH color form of chromogen.

The chromogenic material is preferably microencapsulated or optionally may be dispersed in the carrier liquid in which the microcapsules are dispersed. The chromogenic material is preferably microencapsuled together with the agriculturle active core of the polyvinyl microcapsules.

Typically the majority of the capsules formed by coacervation in the present invention range in size from about 10 nanometers to about 1000 microns, preferably from about 50 nanometers to about 100 microns, and most preferably from about 10 to 50 microns. These capsules typically are of a fairly wide size distribution with substantial quantities of diverse capsule sizes occurring across the range. The particular particle size and/or particle size distribution is not critical to practice of the present invention.

As used herein, "core material" or "core component" is intended to mean all the material encapsulated by the microcapsule wall material forming the internal content of the microcapsule. The agriculture active core material used in the present invention is typically fluid or dispersed oil or solid and can include solvent and other dissolved or dispersed components.

The core material is present in the microcapsule from about 0.1%, from about 1% or even from about 5% by weight based on the total weight of the microcapsule to about 99%, to about 80%, to about 55% or even to about 30%. Preferably, the core material is present in the microcapsule at a level of from about 1 to 99% by weight based on the total weight of the microcapsule, which includes the weight of the encompassing shell material: Typically, the core material is present in an amount of from about 5 to about 90% by weight, based on the total weight of the microcapsule. The respective amount of core material present is not critical to practice of the encapsulation of the present invention. The amount of agriculture active should be sufficient to exhibit the desired beneficial effect on the sites of application.

The agriculture active containing microcapsules of the present invention can be made by conventional coacervation procedures. A polyvinyl alcohol aqueous solution is provided comprising from about 3 to about 25% solids of polyvinyl alcohol. The polyvinyl alcohol is combined with water in a reactor together with the emulsifiable agriculture active component (typically in the form of an oil or dispersion in oil). High shear is applied by means, for example, of a suitable stirring means until the desired emulsion is obtained having the desired particle sizes. The shear and type required can vary as long as the outcome or particle size distribution is achieved. The distribution can be very broad or very narrow depending on the type of performance desired from the end user. Once the desired emulsion is obtained, a source of boron ions such as a 1% solution of Borax salt (sodium tetraborate)

is added incrementally (such as drop-wise) under light stirring to obtain boron ion-crosslinked polyvinyl alcohol microcapsules containing a fragrant core material. The particle size of the capsules can range from 1 micron to 150 microns. The distributions can be bimodal, trimodal or have a very narrow distribution. Preferred milling is to 10-50, more preferably 20 microns with bimodal distribution. The above process occurs at ambient temperature in the absence of added heat input.

Upon the addition of the Borax salt, for instance, the salt dissolves to form boric acid which, in its hydrolyzed form, serves as a crosslinking agent with respective molecules of polyvinyl alcohol via a condensation reaction. While in the presence of water, the crosslinked polyvinyl alcohol microcapsules retain their flexibility, but return to a solid phase upon being dried, resulting in the disintegration of the microcapsule and the release of the core agriculture active material.

Persulfate salt similarly was found to serve as a similar cross-linking agent with respect to polyvinylalcohol. Capsules formed using persulfate salts similarly retained flexibility in the presence of water but returned to a solid phase and upon being dried the capsules disintegrated releasing the core contents, resulting in deposition of the core agricultural material on the site of application.

The microcapsules of the present invention have multiple end uses. For instance, such microcapsules find particular utility in the application of an agriculture active to a substrate in order to, for instance, deliver pest control, or pest control along with color indication of areas protected. In such an embodiment, the microcapsules are applied in the form of an aqueous suspension of the microcapsules by any convenient manner, such as by spraying (with or preferably without the use of propellants), the use of trigger sprayers, aerosols, pump sprayers, atomizers, etc. The composition is preferably applied directly to a substrate or sprayed in the air and permitted to fall or disperse onto the substrate. Once applied, as the aqueous suspension dries, the microcapsules will also dry (causing the polyvinyl alcohol to revert to solid form), whereby the agriculture active core material is caused to be released.

The compositions of the present invention may be formed by any suitable method. For instance, an aqueous dispersion of the microcapsules of the present invention may be combined with suitable adjuvants such as nutrient components. The microcapsules are not dried prior to forming the composition, as such drying would cause the microcapsules to prematurely disintegrate.

As noted previously, the microcapsules of the present invention find utility in agriculture active compositions suitable for application to a wide variety of substrates including plants, crops, soil and plant propagation material. Such compositions typically are comprised of one or more of surfactants, hydrophilic polymers, organic solvents, mono- or polycarboxylic acids, a thickening polymer, a surfactant, and optionally a chromogenic material. Such a composite would generally be comprised of an aqueous solvent system with dispersed microcapsules or comprised of liquid carriers described earlier herein along with the microcapsules.

Suitable surfactants typically are comprised of alkylpolysaccharides, alkyl ethoxylates, alkyl sulfonates, and mixtures thereof, and are generally present in an amount of from about 0.001 to about 0.5% by weight. Hydrophilic polymers optionally may be used to increase the hydrophilicity of the surface to be treated. A variety of hydrophilic polymers may be used, including but not limited to those containing hydrophilic groups such as amine oxide, sulfonate, pyrrolidone, and carboxylate groups, and are generally present in an amount of up to 0.5% by weight. Such polymers generally have a molecular weight of from 10,000 to 1,000,000. Typical organic solvents are generally present in an amount of from about 0.5 to 7% by weight, and may include the various liquid carrier materials described earlier herein, or may include solvents as mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, 3-methoxy-3-methyl-butanol, and mixtures thereof The presence of the organic solvent serves to assist the surfactant in wetting or coating the substrate. Mono- and polycarboxylic acids may optionally be used as well, and may include acetic acid, glycolic acid or beta.-hydroxy propionic acid, citric acid, tartaric acid, succinic acid, glutaric acid, adipic acid, and mixtures thereof. A thickening polymer such as xanthan gum can be employed with advantage in an amount of from about 0.001 to about 0.1% by weight. The composition will further typically be comprised of an aqueous solvent system, which comprises from about 80 to about 99% by weight of the composition. Water-soluble organic solvent components may optionally also be present in minor amounts to aid dispersion, such as lower alcohols including but not limited to methanol, ethanol, isopropanol, n-butanol, iso-butanol, 2-butanol, pentanol, methoxymethanol, methoxyethanol, methoxy propanol, and mixtures thereof.

The identity and/or relative amounts of the above components can be readily determined by one skilled in the art, taking into account factors such as the type of substrate, the manner by which the composition is to be applied, and the identity of the substrate. Indeed, the present invention has applicability in household or general agricultural use.

Such materials employ a variety of components which are well known to those skilled in the art, as confirmed by the following patents, each of which is herein incorporated by reference.

The various products with which the microcapsules of the present invention may be employed include surfactant and emulsifying systems which are well known to those skilled in the art.

The microcapsules of the present invention are further described in the following example which is intended to be merely exemplary and not limiting.

EXAMPLE 1

Boron-ion crosslinked polyvinyl alcohol microcapsules of the present invention are produced as follows. A 1% Borax solution is prepared by adding 198.1 grams of deionized water to a beaker while stirring with a stir bar at room temperature. 2.04 grams of 20 Mule Team Borax Tech 4/200 Mesh (Sodium Tetraborate Decahydrate) is added while stirring. The 1% Borax solution is allowed to mix for 10 minutes or until the material is dissolved and the water clear. A 15.5% polyvinyl alcohol solution is prepared by adding 593.2 grams of deionized water to a water jacketed vessel set to 80° C. The water is stirred with a paddle mixer while 108.6 grams of granular Celvol 523 is added slowly over one minute. The polyvinyl alcohol is allowed to mix and cook at this temperature for 30 minutes before being removed and cooled.

40.37 grams of 15.5% 523 polyvinyl alcohol are added to a 1 kg reactor to which is previously added 200.96 grams distilled water. The mixture is stirred with a 2 inch diameter, 4 point star blade mixer for a period of 5 minutes at 425 RPM. 200.17 grams of GardenTech Sevin Concentrate Bug Killer (TechPac LLC. P.O. Box 24830, Lexington, Ky. 40524) is added while stirring. The agriculture active material is a common insecticide, and is a mixture of Carbaryl (cas 63-25-2) at 22.5% along with Ethanol (cas 57-55-6) and Propylene Glycol. The mixture is milled with the same flat 4 point star blade, 2 inches in diameter at 1500 rpm for a period of 4 minutes to achieve microspheres having a particle size predicted to have a mean at 11 microns, standard deviation of about 14.5 microns and median of about 7.11 microns.

After milling, the star mixer is changed to a paddle mixer and the slurry is allowed to mix at 465 RPM while, 56.69 grams of the 1% Borax solution is added drop-wise over a period of 5 minutes and allowed to finish mixing for another 15 minutes at 700 RPM. Approximately 11 parts by weight of the 1% Borax solution is added to the mixture. The boron-ion crosslinked polyvinyl alcohol microcapsules are formed with expected particle size mean of 11.34 microns, standard deviation of about 13.86 microns and median of about 7.71 microns.

The total time for the preparation of the Celvol 503 and 20 Mule Team Borax solutions is approximately 40 minutes. The microencapsulation procedure can occur at room temperature in about 20 minutes.

The capsules can be collected onto a paper sheet, and the effect studied. The paper will become oil-saturated over a period of one hour, which will confirm that the microcapsules disintegrate upon being dried and exposure to room temperature.

The polyvinyl alcohol was prepared from >92% by wt. acetic acid ethenyl ester polymer with ethanol, <5% by wt. water, <3% by wt. sodium acetate anhydrous, and <1% by wt. methyl alcohol.

EXAMPLE 2

39.72 grams of 15.5% 523 polyvinyl alcohol is added to a 1 kg reactor to which is previously added 198.83 grams distilled water. The mixture is stirred with a 2 inch diameter, 4 point star blade mixer for a period of 5 minutes at 450 RPM. 203.2 grams of Ferti-lome Fruit Tree Spray (Voluntary Purchasing Groups Inc., P.O. Box 460, Bonham, Tex. 75418) is added while stirring. The fruit tree spray is a mixture of Clarified Neem oil (cas 5989-65-1) at 70.0%, Pyrethrins (cas 8003-34-7) at 0.25%, Piperonyl Butoxide (cas51-03-6) at 2.5% and inerts at 27.255. The mixture is milled with the same flat 4 point star blade, 2 inches in diameter at 1300 rpm for a period of 3 minutes to achieve microspheres having a particle size predicted to have a mean at 5.98 microns, standard deviation of about 2.40 microns and median of about 6.01 microns.

After milling, the star mixer is changed to a paddle mixer and the slurry is allowed to mix at 400 RPM while, 78.19 grams of the 1% Borax solution is added drop-wise over a period of 7 minutes and allowed to finish mixing for another 15 minutes at 700 RPM. Approximately 15 parts by weight of the 1% Borax solution is added to the mixture. The boron-ion crosslinked polyvinyl alcohol microcapsules are formed with expected particle size mean of 5.65 microns, standard deviation of about 3.40 microns and median of about 5.38 microns.

The capsules can be collected onto a paper sheet, and the effect studied. The paper will become oil-saturated over a period of one hour, which will confirm that the microcapsules disintegrate upon being dried and exposure to room temperature.

EXAMPLE 3

53.41 grams of 12.5% 523 polyvinyl alcohol are added to a 1 kg reactor to which was previously added 240.69 grams distilled water. The mixture is stirred with a 2 inch diameter, 4 point star blade mixer for a period of 5 minutes at 425 RPM. 125.95 grams of Ferti-lome Fruit Tree Spray (Voluntary Purchasing Groups Inc., P.O. Box 460, Bonham, Tex. 75418) is mixed with 110.16 grams of Norpar 12 from Exxon. A fruit tree spray and Norpar diluent mixture is added to the reactor while stirring. The fruit tree spray is a mixture of Clarified Neem oil (cas 5989-65-1) at 70.0%, Pyrethrins (cas 8003-34-7) at 0.25%, Piperonyl Butoxide (cas51-03-6) at 2.5% and inerts at 27.25%. The mixture is milled with the same flat 4 point star blade, 2 inches in diameter at 1500 rpm for a period of 5 minutes to achieve microspheres having a particle size predicted to have a mean at 35.52 microns, standard deviation of about 14.93 microns and median of about 34.19 microns.

After milling, the star mixer is changed to a paddle mixer and the slurry is allowed to mix at 750 RPM while, 24.22 grams of the 1% Borax solution is added drop-wise over a period of 9 minutes and allowed to finish mixing for another 15 minutes at 750 RPM. Approximately 4 parts by weight of the 1% Borax solution is added to the mixture. The boron-ion crosslinked polyvinyl alcohol microcapsules are formed with expected particle size mean of 33.48 microns, standard deviation of about 15.49 microns and median of about 32.08 microns.

EXAMPLE 4

49.8 grams of 15% 523 polyvinyl alcohol are added to a heated (45° C.) 1 kg reactor to which was previously added 243.1 grams distilled water. The mixture is stirred with a 2 inch diameter, 4 point star blade mixer for a period of 10 minutes at 600. RPM. 115.1 grams of Chlorpyrifos (Jiangsu Fengshan Group Co Ltd. E, 30F, Riyue Mansion, 2 Taiping South Road, Nanjing, Anhui, China 210002), 55.1 grams Xylene (cas1330-20-7), and 66.3 grams of Polyoxyalkylene (Polyglycol) are mixed together at 45° C. 400 rpm for 30 minutes before being added to the reactor. The mixture is milled at 45° C. with the same flat 4 point star blade, 2 inches in diameter at 2000 rpm for a period of 3 minutes to achieve microspheres having a particle size predicted to have a mean at 29.58 microns, standard deviation of about 13.32 microns and median of about 28.46 microns.

After milling, the star mixer is changed to a paddle mixer and the slurry is allowed to mix at 450 RPM while, 53.4 grams of the 1% Borax solution is added drop-wise over a period of 8 minutes and allowed to finish mixing for another 15 minutes at 450 RPM. Approximately 10 parts by weight of the 1% Borax solution is added to the mixture. The boron-ion crosslinked polyvinyl alcohol microcapsules are formed with expected particle size mean of 25.19 microns, standard deviation of about 8.38 microns and median of about 25.05 microns. The entire process was carried out at 45° C.

EXAMPLE 5

50.27 grams of 12.5% 523 polyvinyl alcohol are added to a heated (85° C.) 1 kg reactor to which was previously added 210.36 grams distilled water. The mixture is stirred with a 2 inch diameter, 4 point star blade mixer for a period of 5 minutes at 425 RPM. 240.1 grams of Ferti-lome Azalea, Camellia, Crape Myrtle Spray Insecticide & Fungicide (Voluntary Purchasing Groups Inc., P.O. Box 460, Bonham, Tex. 75418) are added to the reactor while stirring. The Insecticide & Fungicide is a mixture of Malathion (cas 121-75-5) at 7.5%, Pentachloronitrobenzene (cas 82-68-8) at 12.5%, Petroleum distillates (cas 64742-95-6) at 48.6%, 1,2,4-Trimethylbenzene (cas 95-63-6) at 25.6%, Xylene (cas1330-20-7)

at 2.4%, Cumene (cas 98-82-8) at 1.2% and Ethylbenzene (cas 100-41-4) at 0.4%. The mixture is milled at 85° C. with the same flat 4 point star blade, 2 inches in diameter at 1800 rpm for a period of 9 minutes to achieve microspheres having a particle size predicted to have a mean at 22.56 microns, standard deviation of about 8.36 microns and median of about 22.29 microns.

After milling, the star mixer is changed to a paddle mixer and the slurry is allowed to mix at 700 RPM while 3.91 grams of Potassium Persulfate (cas 7727-21-1) from Malinckrodt Baker Inc. Phillipsburg, N.J. 08865 is added to the vessel over 30 seconds. The mixture was allowed to mix for 40 minutes before the heat is removed. The persulfate-ion crosslinked polyvinyl alcohol microcapsules are formed with expected particle size mean of 45.35 microns, standard deviation of about 16.65 microns and median of about 45.29 microns. The entire process is carried out at 85° C. The pH of the final solution was 1.83 at 45.26% solids and viscosity of 516 cps.

The capsules can be collected onto a paper sheet, and the effect studied. The paper will become oil-saturated over a period of one hour, which will confirm that the microcapsules disintegrate upon being dried and exposure room temperature. This effect was also viewed on a microscope slide.

The above descriptions are intended to be merely illustrative of the present invention, and not intended to be limiting thereof. Minor changes and deviations may be made herein without departing from the scope of the invention.

EXAMPLE 6

51.32 grams of 12.5% 523 polyvinyl alcohol are added to a heated (85° C.) 1 kg reactor to which was previously added 240.61 grams distilled water. The mixture is stirred with a 2 inch diameter, 4 point star blade mixer for a period of 5 minutes at 425 RPM. 25.03 grams of Sulfonylurea (cas 35507-37-0 Fisher Scientific) is dissolved in 227.1 grams of Oleocal 112 from Lambent Technologies Corp. (Methyl Ester of Canola oil, cas 67762-38-3) at 69.3° C. for 15 minutes with stirring. The mixture is milled at 85° C. with a flat 4 point star blade, 2 inches in diameter at 2000 rpm for a period of 3 minutes to achieve microspheres having a particle size predicted to have a mean at 24.13 microns, standard deviation of about 9.70 microns and median of about 23.37 microns.

After milling, the star mixer is changed to a paddle mixer and the slurry is allowed to mix at 700 RPM while 4.0 grams of Potassium Persulfate (cas 7727-21-1) from Malinckrodt Baker Inc. Phillipsburg, N.J. 08865 are added to the vessel over 30 seconds. The mixture heating is turned off and allowed to cool naturally. The persulfate-ion crosslinked polyvinyl alcohol microcapsules are formed with expected particle size mean of 24.31 microns, standard deviation of about 9.61 microns and median of about 23.56 microns. The pH of the final solution was 1.81 at 1.28% solids and viscosity of 728 cps. The pH is critical in preventing the breakdown of sulfonylurea and decreasing solubility in the aqueous phase.

The above descriptions are intended to be merely illustrative of the present invention, and not intended to be limiting thereof. Minor changes and deviations may be made herein without departing from the scope of the invention.

The principles, preferred embodiments, and modes of operation of the present invention have been described in the foregoing specification. The invention which is intended to be protected herein, however, is not to be construed as limited to the particular form disclosed, since these are to be regarded as illustrative rather than restrictive. Variations and changes can be made by those skilled in the art without departing from the spirit and scope of the invention.

What is claimed is:

1. A method of delivering an agricultural active to a substrate, comprising applying to said substrate an aqueous composition comprising a suspension of microcapsules in a water phase and comprised of agricultural active, the microcapsules comprising, boron ion or persulfate ion-crosslinked, polyvinyl alcohol microcapsules stable in water and encapsulating the agricultural active and a nonsolvent for the water phase, said microcapsules disintegrating upon drying of said composition subsequent to application of said composition to said substrate.

2. The method of claim 1, wherein said microcapsules contain an agricultural active dispersed in oil as a core material.

3. The method of claim 1, wherein said microcapsules are prepared by a method comprising the steps of:
   (a) providing an aqueous suspension of polyvinyl alcohol having a solids content within the range of about 3 to about 25% by weight;
   (b) combining said aqueous suspension of step (a) with at least one emulsifiable agriculture active component under sufficient applied shear and for a time sufficient to obtain a stable emulsion of said at least one agriculture active component in said aqueous suspension of polyvinyl alcohol; and
   (c) subsequently adding a source of boron or persulfate ions to said emulsion of step (b) in an amount sufficient to crosslink said polyvinyl alcohol to obtain an aqueous mixture of microcapsules.

4. The method of claim 1, wherein said solids content of said aqueous solution in step (a) is about 3 to about 25% by weight.

5. The method of claim 1, wherein said source of boron ions is selected from the group consisting of Borax, sodium tetraborate, disodium tetraboratepentahydrate, disodium tetraborate decahydrate, sodium metaborate, and sodium perborate.

6. The method of claim 1, wherein said source of persulfate ions is selected from the group consisting of alkali peroxymonosulfate, alkali peroxydisulfate, and ammonium peroxydisulfate.

7. The method of claim 1, wherein said source of boron or persulfate ions is present in an amount of from about 0.1 to about 3% by weight.

8. The method of claim 1, wherein said at least one emulsifiable agriculture active component is selected from the oil soluble groups selected from organophosphates, carbamates, formamidine, pyrethroids and sulfonylureas.

9. The method of claim 1, wherein said at least one emulsifiable agriculture active component is present in an amount in the range of about 0.00005 to about 95% by weight.

10. The method of claim 1, wherein said composition comprises a crop protection composition, a soil protection composition, or a hard substrate treating composition.

11. A method of delivering an agricultural active to a substrate wherein a treating solution is applied to a substrate to be protected, wherein said treating solution comprises an aqueous composition comprising a suspension of microcapsules in a water phase and comprised of agricultural active, the microcapsules being formed by coacervation and comprising, boron ion or persulfate ion crosslinked, polyvinyl alcohol microcapsules stable in water and encapsulating a nonsolvent for the water phase together with an effective amount of at least one agricultural active component, said microcapsules disintegrating upon drying said composition subsequent to application of said composition to said substrate.

12. The method of claim 11, wherein said microcapsules contain an agriculture active dispersed in oil as a core material.

13. The method of claim 11, wherein said microcapsules are prepared by a method comprising the steps of:
   (a) providing an aqueous suspension of polyvinyl alcohol having a solids content within the range of about 3 to about 25% by weight;
   (b) combining said aqueous suspension of step (a) with at least one emulsifiable agriculture active component under sufficient applied shear and for a time sufficient to obtain a stable emulsion of said at least one emulsifiable agriculture active component in said aqueous suspension of polyvinyl alcohol; and
   (c) subsequently adding a source of boron or persulfate ions to said emulsion of step (b) in an amount sufficient to cross-link said polyvinyl alcohol to obtain an aqueous mixture of microcapsules.

14. The method of claim 13, wherein said solids content of said aqueous solution in step (a) is about 3 to about 30% by weight.

15. The method of claim 13, wherein said source of boron ions is selected from the group consisting of Borax, sodium tetraborate, disodium tetraborate pentahydrate, disodium tetraborate decahydrate, sodium metaborate and sodium perborate.

16. The method of claim 13, wherein said source of persulfate ions is selected from the group consisting of alkali peroxymonosulfate, alkali peroxydisulfate, and ammonium peroxydisulfate.

17. The method of claim 13, wherein said source of boron ions is present in an amount of from about 0.1 to about 3% by weight.

18. The method of claim 13, wherein said at least one emulsifiable agriculture active component is selected from the group consisting of pesticides, herbicides, or growth regulators.

19. The method of claim 13, wherein said at least one emulsifiable agriculture active component is present in an amount in the range of about 50 to about 95% by weight.

20. The method of claim 13 wherein said agriculture active includes in addition a chromogenic material.

* * * * *